US010597410B2

United States Patent
Santillo et al.

(10) Patent No.: US 10,597,410 B2
(45) Date of Patent: Mar. 24, 2020

(54) INTERMEDIATES AND PROCESS FOR THE PREPARATION OF A CRYSTALLINE FORM OF A TOPICAL ANTI-INFLAMMATORY AGENT

(71) Applicant: DIPHARMA FRANCIS S.R.L., Baranzate (MI) (IT)

(72) Inventors: Niccolo' Santillo, Baranzate (IT); Emanuele Attolino, Baranzate (IT); Davide Brenna, Baranzate (IT); Chiara Vladiskovic, Baranzate (IT); Alessandro Lombardo, Baranzate (IT); Gabriele Razzetti, Baranzate (IT)

(73) Assignee: DIPHARMA FRANCIS S.R.L., Baranzate (MI) (IT)

( * ) Notice: Subject to any disclaimer, the term of this patent is extended or adjusted under 35 U.S.C. 154(b) by 0 days.

(21) Appl. No.: 16/255,956

(22) Filed: Jan. 24, 2019

(65) Prior Publication Data
US 2019/0241585 A1 Aug. 8, 2019

(30) Foreign Application Priority Data

Feb. 2, 2018 (IT) .................. 102018000002347
May 9, 2018 (IT) .................. 102018000005225

(51) Int. Cl.
*C07F 5/04* (2006.01)
*C07F 5/02* (2006.01)
*A61K 9/00* (2006.01)

(52) U.S. Cl.
CPC ............ *C07F 5/025* (2013.01); *A61K 9/0014* (2013.01); *C07F 5/02* (2013.01); *C07F 5/04* (2013.01); *C07B 2200/13* (2013.01)

(58) Field of Classification Search
CPC ....................................... C07F 5/04
See application file for complete search history.

(56) References Cited

U.S. PATENT DOCUMENTS

2017/0152273 A1 6/2017 Merchant et al.
2017/0305936 A1 10/2017 Ceric et al.

FOREIGN PATENT DOCUMENTS

| CN | 107759625 A | | 3/2018 |
| CN | 108341958 A | * | 7/2018 |
| WO | 2017193914 A1 | | 11/2017 |
| WO | 2017203514 A1 | | 11/2017 |

OTHER PUBLICATIONS

Akama T., et al., "Discovery and structure-activity of a novel benzoxaborole anti-inflammatory agent (AN2728) for the potential topical treatment of psoriasis and atopic dermatitis", Biological & Medicinal Chemistry Letters, 19 (2009) 2129-2132.
Barrett A.G.M., et al., "Total Synthesis of the Antifungal Agent Papulacandin D", J. Chem. Soc., Chem. Commun. 1995, 1147-1148.

* cited by examiner

*Primary Examiner* — Matthew P Coughlin
(74) *Attorney, Agent, or Firm* — Silvia Salvadori, P.C.; Silvia Salvadori

(57) ABSTRACT

The present invention relates to a process for the preparation of an inhibitor of phosphodiesterase 4, in particular of phosphodiesterase 4B (PDE4B), and intermediates useful for its preparation.

16 Claims, 2 Drawing Sheets

INTERMEDIATES AND PROCESS FOR THE PREPARATION OF A CRYSTALLINE FORM OF A TOPICAL ANTI-INFLAMMATORY AGENT

This application claims priority to and the benefit of Italian Application No. 102018000002347 filed Feb. 2, 2018. This application also claims priority to and the benefit of Italian Application No. 102018000005225 filed May 9, 2018. The contents of both applications are incorporated herein by reference in their entireties.

FIELD OF THE INVENTION

The present invention relates to a process for the preparation of an inhibitor of phosphodiesterase 4, in particular of phosphodiesterase 4B (PDE4B), and intermediates useful for its preparation.

BACKGROUND 4-((1-Hydroxy-1,3-dihydrobenzo[c][1,2]oxaborol-5-yl)oxy)benzonitrile i.e. Crisaborole, of formula (I),

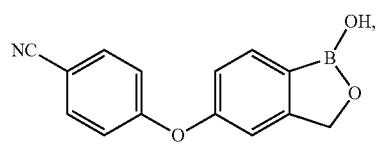

is a non-steroidal topical inhibitor of phosphodiesterase 4 (PDE4), in particular of phosphodiesterase 4B (PDE4B), an enzyme that regulates the inflammation by degradation of adenosine monophosphate (cAMP). PDE4 is hyperactivated in atopic dermatitis and leads to an increase of the symptoms of said disease. Inhibition of PDE4 blocks the release of pro-inflammatory cytokines and in clinical studies Crisaborole showed a significant improvement in pruritus and other symptoms of the disease.

On Dec. 14, 2016, the FDA approved Crisaborole as ointment for topical treatment of atopic dermatitis in adults and children aged two years and more.

Crisaborole is known from U.S. Pat. No. 8,039,451, which claims the compound as such and pharmaceutically acceptable salts thereof. One synthesis of Crisaborole is described in Bioorg. Med. Chem. Lett., 2009, 19, 2129-2132, but the therein disclosed process is rather long and complex (Scheme 1).

Scheme 1

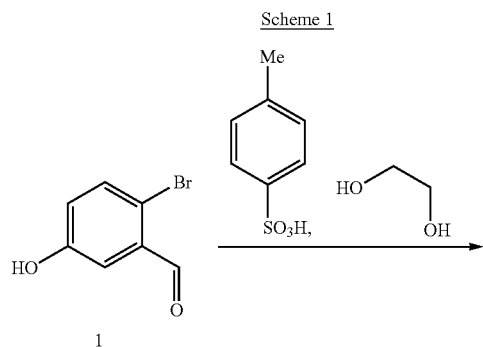

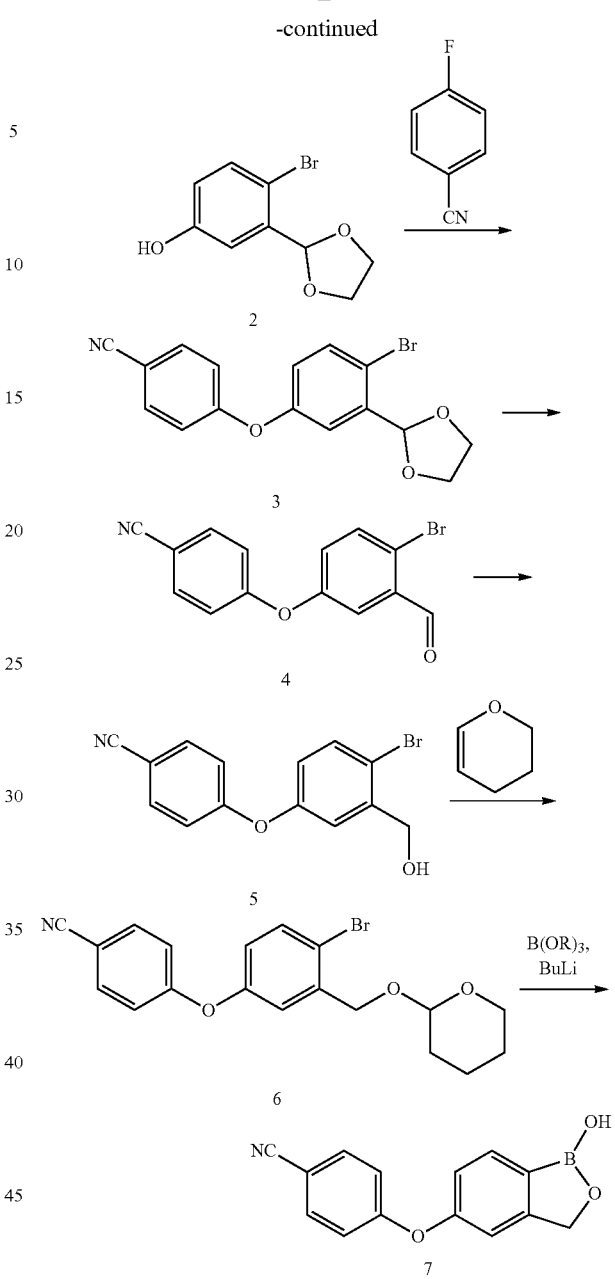

The synthesis comprises the protection of the commercially available aldehyde 1 with ethylene glycol in presence of p-toluenesulfonic acid in toluene to give intermediate 2. The subsequent reaction with commercially available 4-fluorobenzonitrile in DMF provides the acetal 3, which is then deprotected to give aldehyde 4. Intermediate 4 is treated with NaBH$_4$ in methanol to give the benzyl alcohol 5 that is then protected as tetrahydropyranyl (THP) to give compound 6. Crisaborole 7 is finally obtained after lithiation, reaction with an alkylborate and acidic hydrolysis. The yields of these final steps from intermediate 6 are just 37 to 44%. The formation of the boronic acid to give Crisaborole can also be performed starting from the unprotected intermediate 5, but the yields in this case are even lower.

Three crystalline forms of Crisaborole of formula (I) have been disclosed in patent application WO2017/093857 filed by Anacor Pharmaceuticals Inc. on 23 Nov. 2016. A crystalline form, named crystalline Form 1, has been specifically claimed with a XRPD spectrum, wherein the characteristic peaks are found at about 6.0, 12.1, 14.1, and 15.4±0.2° in 2θ, using CuKα (λ=1.54 Å) radiation. According to WO2017/093857, the crystalline Form 1 "was identified as the commercial form and was utilized in Phase 3 studies". The crystalline Form 2 has been used in clinical trials of phase 1 and 2, and according to the inventors the crystalline Form 3 is typically found after rapid evaporation of the solvents, such as ethyl acetate, methyl ethyl ketone or methyl-tert-butyl ether.

WO2017/093857 provides procedures for the preparation of all three crystalline forms of Criaborole of formula (I), but the methods disclosed in the examples for the crystalline Forms 1 and 3 make use of previously obtained seed crystals of Form 1 and Form 3. However, the application is silent about the preparation of said seeds. The authors of the present invention have repeated exactly the procedures reported in WO2017/093857 for the preparation of Form 1 without using any seed crystal and obtained Crisaborole in crystalline Form 2.

Therefore, there remains a need of a simpler and more advantageous alternative method for preparing Crisaborole of formula (I). This new method should in particular consist of fewer synthetic steps, should avoid an extensive use of protecting groups and improve the overall atom economy of the process. Said process should also be cost effective, safe for human and environment, and should use mild reaction conditions in order to obtain Crisaborole of formula (I) in high yields.

In addition, there remains also a need for a procedure for preparing Crisaborole in crystalline Form 1 sufficiently described to be repeated by a person skilled in the art. In addition, there is the need for an environmentally friendly process, which is industrially safe and/or simple, which allows to obtain the desired polymorph in a particularly advantageous manner, in high yields and purity, and which is feasible on an industrial scale.

SUMMARY OF THE INVENTION

In one embodiment, the present invention relates to a process for the preparation of a compound of formula (II)

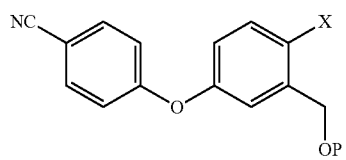

wherein X is a halogen atom,
P is hydrogen or a protective group for the hydroxyl functionality;
comprising the arylation reaction of a compound of formula (III)

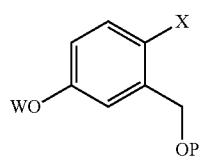

wherein X and P are as defined above and
W is hydrogen or a protective group for the phenolic functionality;
with a compound of formula (IV)

wherein Y is a halogen atom;
in presence of a base and optionally a solvent.

In a further embodiment, the present invention relates to a process for the preparation of Crisaborole crystalline Form 1 that allows to obtain said crystalline Form 1 in an advantageous manner. Surprisingly, this new process of crystallization is also an effective method of preparing highly pure Crisaborole in crystalline Form 1, typically equal to or greater than 99.8% measured by HPLC.

Short Description of the Figures and the Analytical Methods

The crystalline Form 1 of Crisaborole and Crisaborole methyl ester of Form α were characterized by X-ray powder diffraction (XRPD). The water content was determined with Karl Fischer titration.

The XRPD spectra were collected with the D8 Bruker diffractometer at the following operating conditions: Bragg-Brentano geometry, Ni-filtered CuKα radiation (λ=1.54 Å), scanning from 3 to 40° degrees in 2θ, with a step size of 0.02° in 2θ and 0.5 s acquisition for each position.

The $^1$H-NMR spectra were acquired with a Varian Mercury 300 spectrometer controlled by VNMR software 6.1B, operating at a frequency of 300 MHz for the protons.

DETAILED DESCRIPTION OF THE INVENTION

Figure 1:
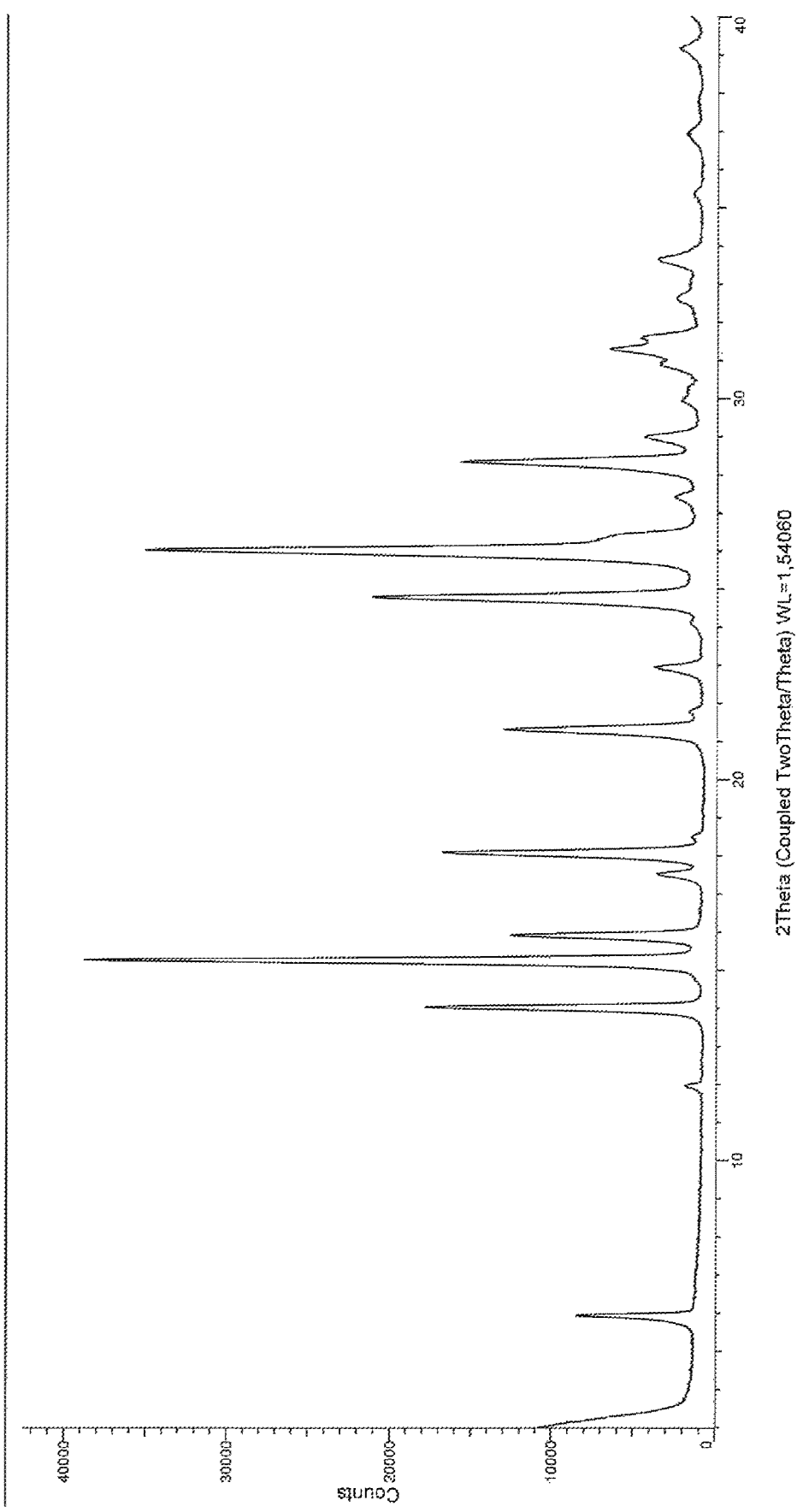
FIG. 1 shows the XRPD spectrum of Crisaborole crystalline Form 1.

In one embodiment, the present invention relates to a process for the preparation of a compound of formula (II)

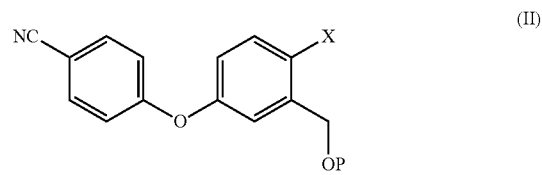

wherein X is a halogen atom,
P is hydrogen or a protective group for the hydroxyl functionality;
comprising the arylation reaction of a compound of formula (III)

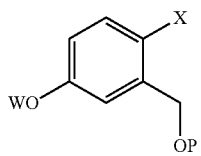

(III)

wherein X and P are as defined above and

W is hydrogen or a protective group for the phenolic functionality;

with a compound of formula (IV)

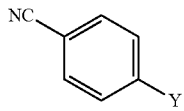

(IV)

wherein Y is a halogen atom;

in presence of a base and optionally a solvent.

X is preferably chlorine, bromine or iodine, and if the case, the conversion of a compound of formula (II) into another compound of formula (II).

A protective group P for the hydroxyl functionality can be a protective group known to the person skilled in the art, for example among those described by T. W. Greene and P. G. M. Wuts in "Protective Groups in Organic Synthesis" Third Edition Wiley, New York 1999. For instance, P may be selected from an ether, for example an allyl ether or an optionally substituted alkylphenyl ether, such as benzyl or p-methoxybenzyl; an acetal, such as methoxymethyl (MOM), tetrahydropyranyl (THP), 2-methoxyethoxymethyl (MEM); or a silyl group.

A protective group W for the phenolic function may be a silyl group, for example an $C_1$-$C_6$ alkyl silyl, an aryl silyl or an aralkyl silyl.

The term "$C_1$-$C_6$ alkyl" refers to a straight or branched hydrocarbon chain radical, consisting solely of carbon and hydrogen atoms, having from one to six carbon atoms. The "$C_1$-$C_6$ alkyl" group is preferably a linear or branched $C_1$-$C_4$ alkyl group.

The term "aryl" represents a mono or bicyclic aromatic ring system of, respectively, 6, 9 or 10 atoms, such as benzene, indene and naphthalene and includes also indan and tetrahydronaphthalene.

The term "aralkyl" represents an aryl-$C_1$-$C_6$ alkyl, wherein aryl and $C_1$-$C_6$ alkyl are as defined above. Examples of aralkyls are benzyl or 2-phenylethyl.

The silyl protective groups, when used as protective groups for P or W, can be a $C_1$-$C_6$ alkyl silyl, an aryl silyl or an aralkyl silyl group, for example a tri-($C_1$-$C_6$)-alkyl silyl or a tri-aryl-silyl, in particular trimethylsilyl, triethylsilyl, triisopropylsilyl, dimethylisopropylsilyl, tert-butyldimethylsilyl, diphenylmethylsilyl, triphenylsilyl and tribenzylsilyl. Preferably, the silyl group is trimethylsilyl, triethylsilyl or tert-butyldimethylsilyl, more preferably trimethylsilyl.

Y is preferably fluorine or chlorine.

A compound of formula (II) may be converted into another compound of formula (II) according to known methods. For example, a compound of formula (II), wherein P is hydrogen, can be converted into another compound of formula (II), wherein P is a protective group for the hydroxyl functionality, according to methods well known in the art.

Vice versa, a compound of formula (II), wherein P is a protective group for the hydroxyl functionality, can be deprotected into a compound of formula (II), wherein P is hydrogen, according to well known methods for the deprotection of the hydroxylic functions.

The base used in the arylation step in the present invention may be an organic or inorganic base.

In particular, the organic base may be selected from the group comprising a secondary amine or a tertiary amine, such as diisopropylamine or diisopropylethylamine (DIPEA).

An inorganic base is typically a hydroxide, a carbonate, a hydrogen carbonate, or a phosphate of an alkali metal or of an alkaline earth metal. Examples of inorganic bases are sodium hydroxide, potassium hydroxide, magnesium hydroxide or calcium hydroxide, sodium carbonate, potassium carbonate, magnesium carbonate or calcium carbonate, sodium hydrogen carbonate, potassium hydrogen carbonate, magnesium hydrogen carbonate or calcium hydrogencarbonate, sodium phosphate, potassium phosphate, magnesium phosphate or calcium phosphate. A preferred base is potassium carbonate.

The arylation reaction can be carried out in the presence of a solvent, such a dipolar aprotic solvent, typically dimethylformamide, dimethylacetamide, acetonitrile, or dimethylsulfoxide; an ether, typically tetrahydrofuran or dioxane; water; or a mixture of two or more, preferably two or three, of the above mentioned solvents. Preferably, the reaction is carried out in dimethylsulfoxide.

The reaction between a compound of formula (III) and a compound of formula (IV) can be carried out at a temperature ranging between approximately 20° C. and the reflux temperature of the solvent, preferably between about 70° C. and 130° C., more preferably between about 70° C. and about 110° C., for example at about 80° C., 90° C., 95° C., 100° C. or 105° C.

In a particularly preferred embodiment of the present invention, the reaction between a compound of formula (III) and a compound of formula (IV) can be performed in dimethylsulfoxide, using potassium carbonate as a base at a temperature ranging between about 70 and about 110° C., for example at 80° C., 90° C., 95° C., 100° C. or 105° C.

A compound of formula (IV) can be used in equimolar amounts or in molar excess with respect to the compound of formula (III). Preferably, it can be used in a range of between about 1.01 to 2 moles, more preferably between about 1.01 and 1.50 moles of the compound of formula (IV) per mole of compound of formula (III).

The arylation reaction of a compound of formula (III) with a compound of formula (IV) can be performed in three different ways.

1) The arylation reaction of a compound of formula (III) with a compound of formula (IV) proceeds with high selectivity, when X and Y are as defined above, W is hydrogen and P is a protecting group for the hydroxyl functionality.

2) The authors of the present invention have found that even when W and P are hydrogen and hence both hydroxyl functionalities are unprotected, the arylation reaction proceeds with good selectivity to give the compound of formula (II). In specific, the selectivity ranges between 50% and 86%. The possible reaction impurities are the compounds of formula (V) and of formula (VI)

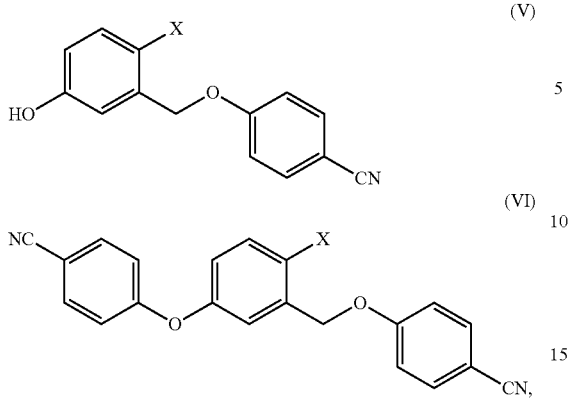

wherein X is as defined above. The impurity of formula (V) is formed by arylation of the benzyl alcohol rather than that of the phenol and the impurity of formula (VI) is formed by arylation of both hydroxyl groups.

In a further embodiment, the present invention relates to a process for the preparation of a compound of formula (II), wherein X is as defined above and P is hydrogen, comprising the arylation reaction of a compound of formula (III), wherein W and P are hydrogen, with a compound of formula (IV), wherein Y is as defined above, in the presence of a base and optionally a solvent, and wherein the base and the optional solvent are as above defined.

3) A person skilled in the art expects that no arylation reaction of a compound of formula (III) may occur with a compound of formula (IV), wherein X and Y are as defined above, W is a silyl group and P is a protecting group for the hydroxyl functionality. However, the authors of the present invention have surprisingly found that the arylation reaction at the conditions of the present invention proceeds with good yields and selectivity that varies between 80% and 92% to give a compound of formula (II), despite both hydroxyl functionalities of W and P are protected, in particular when W and P are trimethylsilyl.

Therefore, in a further embodiment, the present invention relates to a process for the preparation of a compound of formula (II), wherein X is as defined above and P is hydrogen, comprising the arylation step of a compound of formula (III), wherein X is as defined above and W and P are trimethylsilyl, with a compound of formula (IV), wherein Y is as defined above, in the presence of a base and optionally a solvent. The base and the optional solvent are as above defined.

In a preferred embodiment, the reaction is carried out in dimethylsulfoxide, with potassium carbonate as a base at a temperature ranging between approximately 80° C. and about 110° C.

A compound of formula (II):

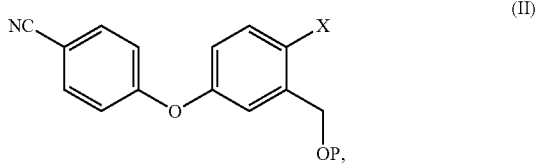

wherein X is a halogen atom, preferably chlorine, bromine or iodine atom, more preferably bromine, and P is a silyl ether group, preferably a trimethylsilyl group, is a new compound and is a further embodiment of the present invention.

A compound of formula (III):

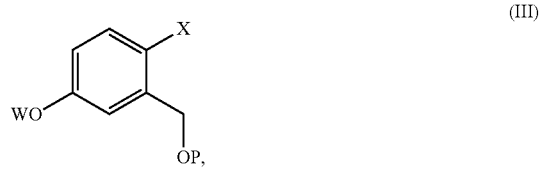

wherein X is a halogen atom, preferably chlorine, bromine or iodine atom, more preferably bromo, and W and P are silyl ether groups, preferably trimethylsilyl groups, is new and is a further embodiment of the present invention.

A compound of formula (III), wherein X is bromine and W and P are trimethylsilyl can be prepared starting from a compound of formula (III), wherein W and P are hydrogen, by conventional silylation reaction of the hydroxyl function. For example, the compound of formula (III), wherein W and P are hydrogen, can be treated with trimethylsilyl chloride, trimethylsilyl bromide in the presence of a base or with 1,1,1-trimethyl-N-(trimethylsilyl)silanamine, optionally in the presence of a solvent.

The base in the preparation of a compound of formula (III), wherein X is bromine and W and P are trimethylsilyl, can be an organic or an inorganic base. The organic base can be a tertiary amine such as triethylamine. The inorganic base is typically a hydroxide, a carbonate, hydrogen carbonate, or a phosphate of an alkali metal or alkaline earth metal. Examples of inorganic bases are sodium hydroxide, potassium hydroxide, magnesium hydroxide or calcium hydroxide, sodium carbonate, potassium carbonate, magnesium carbonate or calcium carbonate, sodium hydrogen carbonate, potassium hydrogen carbonate, magnesium hydrogen carbonate or calcium hydrogencarbonate, sodium phosphate, potassium phosphate, magnesium phosphate or calcium phosphate. Preferably, the base is an organic base, more preferably the base is triethylamine.

The silylation reaction can be carried out in the presence of a solvent, for example in a dipolar aprotic solvent, typically dimethylformamide, dimethylacetamide, acetonitrile, or dimethylsulfoxide; in an ethereal solvent, typically tetrahydrofuran or dioxane; in an apolar aprotic solvent, such as hexane or toluene; or in a mixture of two or more, preferably two or three, of the solvents listed above. A preferred solvent is toluene or a dipolar aprotic solvent, typically dimethylformamide, dimethylacetamide, acetonitrile, or dimethylsulfoxide.

The silylation reaction can be carried out at a temperature between about −10° C. and the reflux temperature of the solvent, preferably between about 0° C. to about 50° C., for instance between about 0° C. to about 15° C., to about 25° C., to about 35° C. or to about 45° C.

A compound of formula (III), wherein X is as defined above and W and P are hydrogen, can be prepared by reducing a compound of formula (VII)

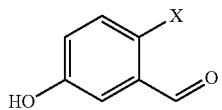

(VII)

wherein X is as defined above, and if desired, a compound of formula (III) can be converted into another compound of formula (III), according to known methods, for instance as described herein.

The reduction of the compound of formula (VII) can be carried out according to methods well known to the person skilled in the art, for example using a hydride as reducing agent in a solvent. The hydride is for example lithium aluminium hydride or sodium borohydride. The reduction can be performed in a solvent, for example an ether. Preferably, the reduction is carried out using lithium aluminium hydride or sodium borohydride in a solvent, for example a di-($C_1$-$C_6$-alkyl) ether or tetrahydrofuran (THF), wherein the "$C_1$-$C_6$ alkyl" is as defined above The compound of formula (VII) is commercially available.

A compound of formula (IV) is commercially available or can be prepared according to known methods.

A compound of formula (II) obtained in accordance with the present invention can be advantageously used in the synthesis of Crisaborole of formula (I), for example according to the procedures reported in U.S. Pat. No. 8,039,451 or in Bioorg. Med. Chem. Left, 2009, 19, 2129-2132.

In a further embodiment, the present invention relates to a process for preparing Crisaborole of formula (I) starting from a compound of formula (II). The conversion of a compound of formula (II) into Crisaborole of formula (I) can be performed by reacting the compound of formula (II) in a solvent with a boric ester, for example with trimethyl borate, triethyl borate or triisopropylborate, preferably with triisopropylborate, and a strong base, for example an organolithium reagent, such as methyllithium, n-butyllithium, sec-butyl lithium, tert-butyllithium, hexyllithium or phenyllithium, forming the benzoxaborole. The reactions can be carried out in a solvent at low temperatures, for example at −70° C., −75° C. or at lower temperatures, preferably at about −78° C. The solvent for example can be an ethereal solvent, typically tetrahydrofuran or diethyl ether; an alkane, typically pentane, hexane or heptane; or a mixture of two or more, for example two or three, of the solvents mentioned above. Preferably, the reaction is carried out in tetrahydrofuran or in a mixture of tetrahydrofuran and hexane.

The possible impurities of formula (V) and of formula (VI)

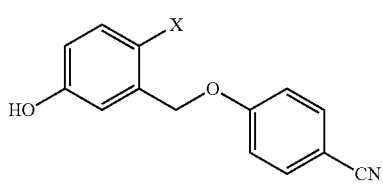

(V)

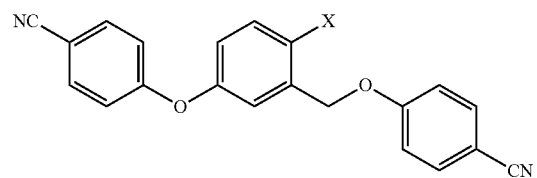

(VI)

wherein X is as defined above, which can be either formed by arylation of the benzyl alcohol instead of the phenol or by arylation of both the hydroxyls during the reaction between a compound of formula (III) and (IV), treated with a boric ester in the presence of a strong base can form the compounds of formula (VIII) and of formula (IX):

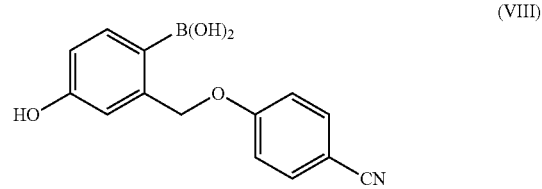

(VIII)

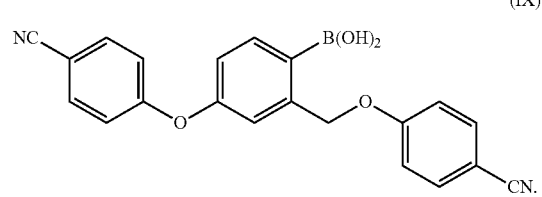

(IX)

The inventors of the present invention have found that Crisaborole prepared according to the present process has a chemical purity, evaluated by HPLC at 254 nm, equal to or greater than 99.8% (Area %), preferably equal to or greater than 99.9%, more preferably equal to or greater than 99.97%, and wherein each impurity is typically present in a percentage equal to or less than 0.1%, for instance in a percentage equal to or lower than 0.05%, preferably equal to or less than 0.03%, more preferably equal to or less than 0.01%. The compounds of formula (VIII) or (IX) as impurities are typically present in a percentage equal to or less than 0.1%, preferably lower than 0.05%, for example at 0.03%, 0.01%, 0.005%, 0.001%, or 0.0005%.

In a further embodiment, the present invention relates to the use of a compound of formula (II) as defined above and obtained according to the present invention, as intermediate in the preparation of Crisaborole of formula (I).

In a further embodiment, the present invention relates to a process for the preparation of Crisaborole of formula (I), comprising the use of a compound of formula (II) as defined above and prepared according to the method described in the present invention.

It has also been surprisingly found that the conversion of a compound of formula (II), wherein X is bromine and P is trimethylsilyl, into Crisaborole of formula (I) proceeds with a yield that varies between 82% and 92%. These yields are much higher than the yields achieved following the previously disclosed procedure, wherein the hydroxyl functionality is protected with a tetrahydropyranyl (THP) group: starting from the THP-protected intermediate as described in Biorg. Med. Chem. Lett. 2009, 19, 2129-2132, Crisaborole of formula (I) is obtained only with yields of 44% as reported in the literature and as also confirmed by the inventors of the present invention.

Therefore, in a further embodiment, the present invention relates to a process for the preparation of Crisaborole of formula (I), comprising the use of a compound of formula (II), wherein X is bromine and P is trimethylsilyl, obtained according to the process described in the present invention.

In a further embodiment, the present invention relates to the use of a compound of formula (III) as defined above and obtained according to the present invention, as intermediate in the preparation of Crisaborole of formula (I).

In a further embodiment, the present invention relates to a process for the preparation of Crisaborole of formula (I), comprising the use of a compound of formula (III) as defined above and prepared according to the method described in the present invention.

In a further embodiment, the present invention relates to new process for the preparation of Crisaborole in crystalline Form 1 having an XRPD spectrum comprising peaks falling at about 6.0, 12.1, 14.1, and 15.4±0.2° in 2θ, comprising:
  i) hydrolizing of Crisaborole $C_1$-$C_5$ alkyl ester of formula (X)

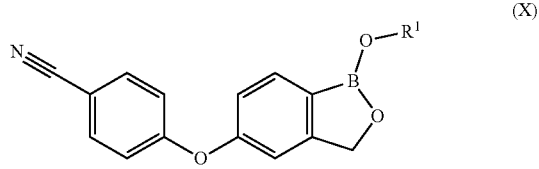

(X)

wherein $R^1$ is a $C_1$-$C_5$ alkyl group.

The $C_1$-$C_5$ alkyl group in $R^1$, which can be linear or branched, is preferably a $C_1$-$C_4$ alkyl group, such as methyl, ethyl, propyl, isopropyl, butyl, more preferably methyl or isopropyl.

Figure 2:
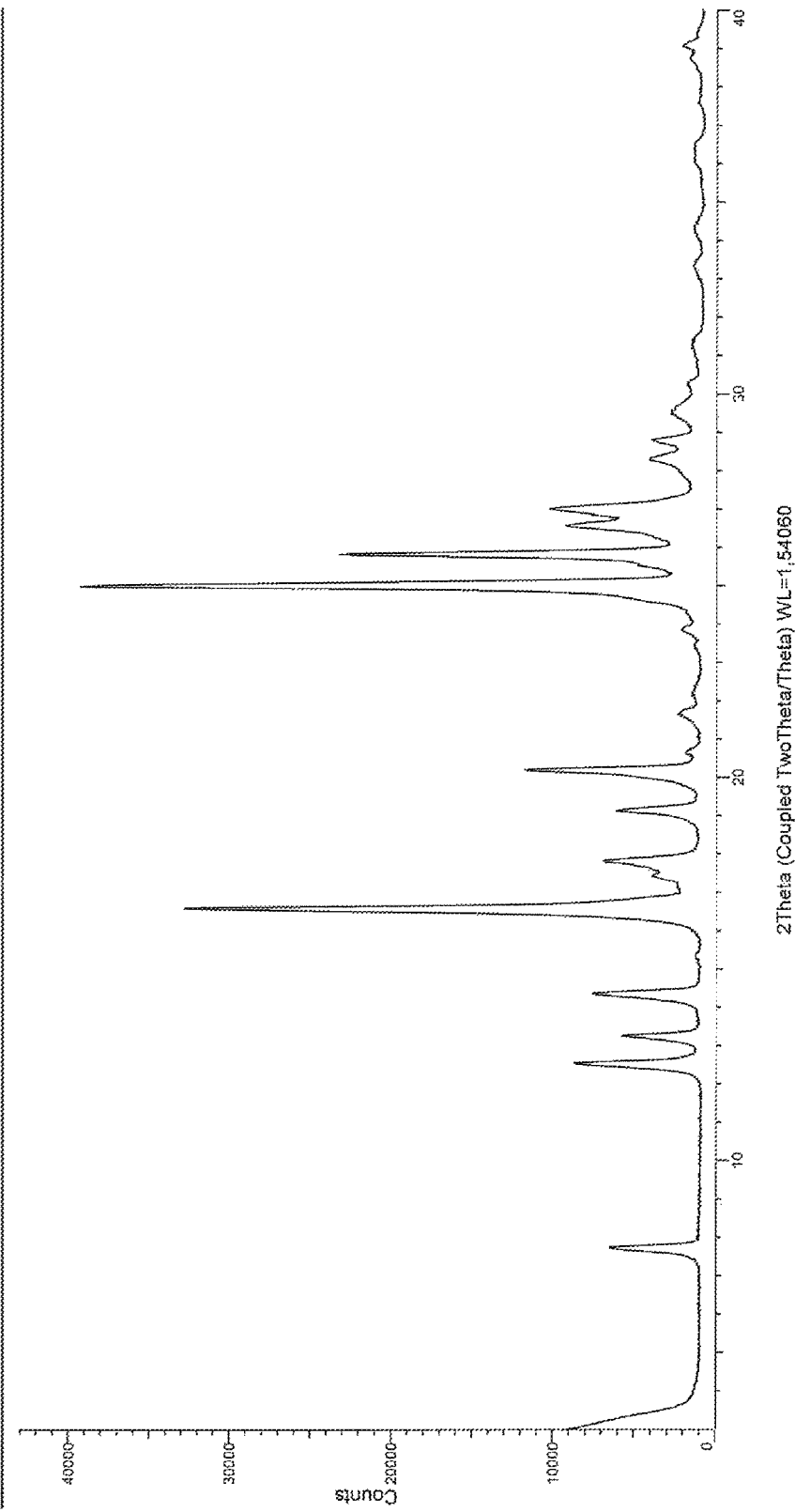
FIG. 2 shows the XRPD spectrum of Crisaborole methyl ester crystalline Form α.

Crisaborole $C_1$-$C_5$ alkyl ester of formula (X) can be for example Crisaborole methyl ester in crystalline Form α having an XRPD spectrum as shown in FIG. 2, wherein characteristic peaks are observed at about 14.1, 16.2, 19.8, 24.7, and 26.6±0.2° in 2θ.

Preferably, Crisaborole methyl ester in crystalline Form α has an XRPD spectrum as shown in FIG. 2, wherein characteristic peaks are observed at about 7.4, 12.2, 13.0, 14.1, 16.2, 17.6, 18.8, 19.8, 24.7, 25.5, and 26.6±0.2° in 2θ.

The hydrolysis of Crisaborole $C_1$-$C_5$ alkyl ester of formula (X) can be carried out by treating the Crisaborole $C_1$-$C_5$ alkyl ester of formula (X) with water. For example, the Crisaborole $C_1$-$C_5$ alkyl ester of formula (X), in particular the Crisaborole methyl ester in crystalline Form α, can be suspended in water, preferably at a temperature between about 0° C. and 60° C., preferably between about 10 and 50° C. for example at 15° C., 20° C., 25° C., 30° C., 40° C. or 45° C., providing Crisaborole in crystalline Form 1 having an XRPD spectrum, wherein the most intense peaks fall at about 6.0, 12.1, 14.1, and 15.4±0.2° in 2θ.

In particular, the inventors of the present invention have found that the hydrolysis of Crisaborole $C_1$-$C_5$ alkyl ester of formula (X) can occur even by exposing Crisaborole $C_1$-$C_5$ alkyl ester of formula (X) to air. The presence of moisture already leads to Crisaborole in crystalline Form 1 having an XRPD spectrum, wherein the most intense peaks are observed at about 6.0, 12.1, 14.1, and 15.4±0.2° in 2θ.

Alternatively, the hydrolysis can be carried out by suspending Crisaborole $C_1$-$C_5$ alkyl ester of formula (X) in a $C_5$-$C_9$ alkane or in a mixture of $C_5$-$C_9$ alkane and a $C_1$-$C_6$ alkyl carboxylic acid ester, stirring the suspension under an atmosphere containing moisture at a temperature between about −20° C. and the boiling temperature of the solvent or the mixture of solvents, preferably at a temperature between about −20 and 60° C., more preferably between about 20° C. and 40° C., for example at 25° C. or at 35° C.

The $C_5$-$C_9$ alkane, which can be linear or branched, is in particular hexane or heptane.

The carboxylic acid is preferably a $C_1$-$C_6$ alkyl carboxylic acid, for example acetic acid, propionic or butyric acid.

The $C_1$-$C_6$ alkyl ester of a carboxylic acid, preferably of a $C_1$-$C_6$ alkyl carboxylic acid, wherein the $C_1$-$C_6$ alkyl group may be linear or branched, is more preferably a $C_1$-$C_4$ alkyl ester of a $C_1$-$C_4$ alkyl carboxylic acid, for example methyl acetate, ethyl acetate, propyl acetate, isopropyl acetate or butyl acetate, preferably ethyl acetate.

Typically the ratio of a mixture of a $C_5$-$C_9$ alkane and a $C_1$-$C_6$ alkyl ester of a carboxylic acid is 1:1 (volume: volume, v:v) or higher, preferably between about 10:1 (v:v) and 1:1 (v:v).

The suspension of Crisaborole $C_1$-$C_5$ alkyl ester of formula (X) can be maintained under stirring, preferably for at least one hour, more preferably for at least 6 hours, typically for at least 6 to 12 hours, or for at least 24 hours or at least 48 hours at a temperature between about −20° C. and the boiling temperature of the solvent or the mixture of solvents, preferably at a temperature ranging between approximately 20° C. and 60° C., for instance at about 20° C., 30° C., 40° C. or 50° C.

To increase the yield of the solid of Crisaborole in crystalline Form 1, the suspension of Crisaborole $C_1$-$C_5$ alkyl ester of formula (X) may be cooled down to a temperature lower than or equal to about 20° C., for example to a temperature of less than 0° C. or between 0° C. and 5° C. The cooling can be performed slowly, for example at a speed at approximately 0.1° C./minute to 0.4° C./minute.

The recovery of the solid consisting in Crisaborole in crystalline Form 1 can be carried out according to known techniques, for example by filtration or by centrifugation, preferably by filtration.

Crisaborole in crystalline Form 1 thus obtained has a water content comprised between 0 and approximately 1% (by weight), preferably between about 0.01 and 0.1%, preferably approximately 0.07%, so that it can be defined substantially anhydrous.

The size of the crystals of Crisaborole in crystalline Form 1, as obtainable according to the invention is characterized by a D50 value between about 25 and 250 μm. If desired, the particle sizes may be reduced by micronisation or milling.

Crisaborole $C_1$-$C_5$ alkyl ester of formula (X) can be obtained by a process comprising:
  ii) forming a solution of Crisaborole of formula (I) in a $C_1$-$C_5$ alcohol or in a mixture of solvents comprising a $C_1$-$C_5$ alcohol;
  iii) cooling and/or concentrating the solution and recovering Crisaborole $C_1$-$C_5$ alkyl ester of formula (X)

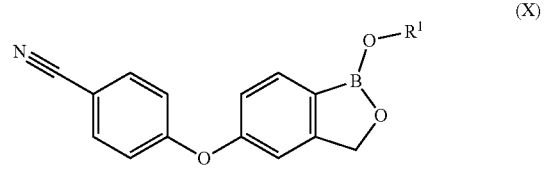

(X)

wherein $R^1$ is defined as above.

The formation of Crisaborole $C_1$-$C_5$ alkyl ester of formula (X) in step (ii) and (iii) are preferably carried out in anhydrous conditions. Typically, the anhydrous conditions are conditions wherein the water content, established by Karl Fischer titration, is equal to or lower than 0.1%, preferably equal to or lower than 0.05%, for instance 0.04%, 0.03%, 0.02%, 0.01%, 0.007%, 0.005%. or 0.001%. The formation of the $C_1$-$C_5$ alkyl ester of formula (X) can be driven by azeotropic distillation of the water produced or using a dehydrating agent, for instance $MgSO_4$ or molecular sieves.

Crisaborole of formula (I) used as starting material in step (ii) of the process described above can be Crisaborole in any solid or not solid form, even a crude reaction mixture comprising Crisaborole of formula (I). For instance, the starting material can be Crisaborole obtained according to the herein presented process, by the procedures disclosed in U.S. Pat. No. 8,039,451, or be one of the crystalline forms of Crisaborole disclosed in WO2017/093857, or can be Crisaborole obtained directly from a reaction mixture.

A $C_1$-$C_5$ alcohol is typically a linear or branched $C_1$-$C_5$ alcohol or a mixture of said alcohols, for example two or three alcohols. A $C_1$-$C_5$ alcohol is preferably a $C_1$-$C_3$ alcohol, such as methanol, ethanol, n-propanol or isopropanol, more preferably methanol or isopropanol.

The mixture of solvents comprising a $C_1$-$C_5$ alcohol may also contain one or more, typically one, two or three solvents selected from polar aprotic solvents, such as dimethylformamide or acetonitrile; ethers, such as diethyl ether, methyl-tert-butylether or tetrahydrofuran; ketones, for example methyl ethyl ketone, methyl isobutyl ketone or acetone; apolar aprotic solvents, such as hexane, heptane, toluene or xylene; esters; chlorinated solvents, for example dichloromethane ($CH_2Cl_2$), chloroform or chlorobenzene; or $C_1$-$C_6$ alkyl esters of a carboxylic acid. Preferred additional solvents are $C_1$-$C_6$ alkyl esters of a carboxylic acid, more preferably of a $C_1$-$C_6$ alkyl carboxylic acid, wherein the $C_1$-$C_6$ alkyl group can be linear or branched, even more preferably $C_1$-$C_4$ alkyl esters of a $C_1$-$C_4$ alkyl carboxylic acid, for example methyl acetate, ethyl acetate, propyl acetate, isopropyl acetate or butyl acetate, preferably ethyl acetate. The $C_1$-$C_6$ alkyl carboxylic acid is for example acetic acid, propionic or butyric acid. Typically, the volumetric ratio between the $C_1$-$C_6$ alkylester of a carboxylic acid and the $C_1$-$C_5$ alcohol in a mixture for step (ii) of the present invention is comprised between 10:1 and 1:10, preferably about 1:1.

If necessary, the dissolution of Crisaborole in step ii) can be carried out at room temperature or by heating the mixture up to the reflux temperature of the solvent or the mixture of solvents.

The cooling of the solution in step (iii) can be carried out according to known methods. For example, it can be carried out by cooling down the solution to room temperature or to about 0-5° C.

The concentration of the solution in step (iii) can be performed according to known methods. For example, the reaction mixture can be concentrated to about half the volume or less.

Optionally, a previously obtained seed crystal of Crisaborole $C_1$-$C_5$ alkyl ester of formula (X) can be added in step iii).

The solid obtained in step iii), consisting in Crisaborole $C_1$-$C_5$ alkyl ester of formula (X), for example Crisaborole methyl ester in crystalline Form α, can be isolated according to known techniques, for example by filtration or centrifugation, preferably by filtration.

In a further embodiment, the present invention relates to the preparation and isolation of a Crisaborole $C_1$-$C_5$ alkyl ester of formula (X), for example Crisaborole methyl ester; Crisaborole ethyl ester; Crisaborole propyl ester; Crisaborole isopropyl ester; Crisaborole butyl ester or Crisaborole methyl ester in crystalline Form α, from Crisaborole.

For example, the preparation and isolation of a compound of formula (X) can be carried out according to the conditions as described above for steps (ii) and (iii).

In a further embodiment, the present invention relates to the compound Crisaborole $C_1$-$C_5$ alkyl ester of formula (X)

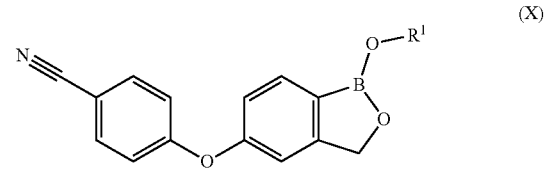

(X)

wherein $R^1$ is a $C_1$-$C_5$ alkyl group.

The $C_1$-$C_5$ alkyl group of $R^1$ can be either linear or branched and is preferably a $C_1$-$C_4$ alkyl group, such as methyl, ethyl, propyl, isopropyl, butyl, more preferably methyl or isopropyl.

Preferred Crisaborole $C_1$-$C_5$ alkyl esters of formula (X) are selected from:
Crisaborole methyl ester;
Crisaborole ethyl ester;
Crisaborole propyl ester;
Crisaborole isopropyl ester; and
Crisaborole butyl ester.

Particularly preferred compounds of formula (X) are selected from:
Crisaborole isopropyl ester; or
Crisaborole methyl ester in crystalline Form α has the XRPD spectrum as shown in FIG. 2, wherein the characteristic peaks are observed at about 14.1°, 16.2°, 19.8°, 24.7°, and 26.6°±0.2° in 2θ.

Preferably, Crisaborole methyl ester in crystalline Form α has an XRPD spectrum as shown in FIG. 2, wherein the characteristic peaks are observed at about 7.4°, 12.2°, 13.0°, 14.1°, 16.2°, 17.6°, 18.8°, 19.8°, 24.7°, 25.5°, and 26.6°±0.2° 2θ.

In a further embodiment, the present invention relates to the use of Crisaborole $C_1$-$C_5$ alkyl ester of formula (X) as defined above in a process for preparing Crisaborole crystalline Form 1 with an XRPD spectrum, wherein the most intense peaks are observed at about 6.0, 12.1, 14.1, and 15.4±0.2° in 2θ.

In a further embodiment, the present invention relates to to the use of Crisaborole $C_1$-$C_5$ alkyl ester of formula (X) as defined above in a process for preparing a pharmaceutical composition comprising Crisaborole of formula (I) and at least one pharmaceutically acceptable carrier or vehicle.

In a preferred embodiment, the pharmaceutical composition comprises compounds of formula (VIII) or (IX)

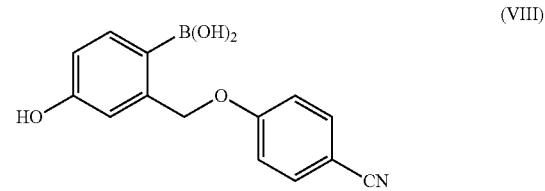

(VIII)

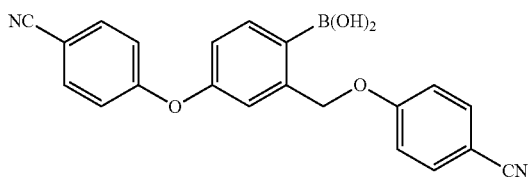

(IX)

as impurities in a percentage equal to or less than 0.1% (compared to Crisaborole of formula (I) and evaluated by HPLC at 254 nm), preferably lower than 0.05%, for example at about 0.03%, 0.01%, 0.005%, 0.001%, or 0.0005%.

The term "pharmaceutically acceptable carrier" or "pharmaceutically acceptable vehicle" refers to any formulation or carrier medium that provides the appropriate delivery of an effective amount of Crisaborole of formula (I), without interfering with the effectiveness of the activity of Crisaborole of formula (I), and that is sufficiently non-toxic to the treated patient. Examples of formulation or carriers can be found in Remington, the Science and Practice of Pharmacy, 22nd Edition, The pharmaceutical Press, London, Philadelphia, 2013.

In a preferred embodiment, the pharmaceutical composition comprising Crisaborole of formula (I) and at least one pharmaceutically acceptable carrier or vehicle is a topical pharmaceutical composition, wherein the composition is formulated as a simple solution, lotion, cream, gel, ointment, or paste.

For instance, the topical pharmaceutical composition can be a non-aqueous topical ointment having a level of Crisaborole of formula (I) at 2% (weight). The non-aqueous topical ointment may further contain one or more excipients selected from petrolatum, propylene glycol, glycerol, mono- and di-glycerides, paraffin wax, ethylhexyl hydroxystearate, butylated hydroxytoluene, and sodium calcium edetate.

For instance, the topical pharmaceutical composition can be an aqueous topical ointment or cream having a level of Crisaborole of formula (I) from 0.2 to 5% (weight). The topical ointment or cream may further contain one or more excipients selected from petrolatum propylene glycol, glycerol, mono- and di-glycerides, oleyl alcohol, benzyl alcohol, diisopropyl adipate, glyceryl monostearate, octyldodecanol, and disodium edetate.

The pharmaceutical composition can be manufactured in several known different ways, for instance according to the procedures disclosed in Remington, the Science and Practice of Pharmacy, 22nd Edition, The pharmaceutical Press, London, Philadelphia, 2013. For example, the pharmaceutical composition can be manufactured by well-known mixing or blending procedures of Crisaborole of formula (I) with at least one pharmaceutically acceptable carrier or vehicle.

The non-aqueous topical ointment comprising Crisaborole of formula (I) may be prepared by mixing one or more excipients selected from petrolatum, mono- and di-glycerides, paraffin wax, butylated hydroxytoluene and combining said mixture with a mixture comprising propylene glycol, sodium calcium edetate and Crisaborole of formula (I), preferably Crisaborole in crystalline form 1 having an XRPD spectrum comprising peaks falling at 6.0, 12.1, 14.1, and 15.4±0.2° in 2θ.

Alternatively, the non-aqueous topical ointment comprising Crisaborole of formula (I) may be prepared by mixing one or more excipients selected from petrolatum, oleyl alcohol, ethylhexyl hydroxystearate and Crisaborole of formula (I), preferably Crisaborole in crystalline form 1 having an XRPD spectrum comprising peaks falling at 6.0, 12.1, 14.1, and 15.4±0.2° in 2θ.

The aqueous topical cream comprising Crisaborole of formula (I) may be prepared by mixing one or more excipients selected from oleyl alcohol, benzyl alcohol, diisopropyl adipate, glyceryl monostearate, octyldodecanol, butylated hydroxytoluene, water and Crisaborole of formula (I), preferably Crisaborole in crystalline form 1 having an XRPD spectrum comprising peaks falling at 6.0, 12.1, 14.1, and 15.4±0.2° in 2θ.

If colour and/or flavours are used they may be added at any stage of the process.

The following examples further illustrate the invention.

Example 1: Synthesis of
2-Bromo-5-hydroxy-benzyl Alcohol of Formula
(III)

9.00 g (249 mmol) of NaBH$_4$ are suspended under nitrogen atmosphere in 300 mL of THF. The suspension is cooled down to 0° C. and 100 g (497 mmol) of 2-bromo-5-hydroxy benzaldehyde of formula (VII) in 200 mL of THF are added over about an hour while maintaining the temperature below 15° C. The mixture is allowed to reach room temperature within one hour, then cooled down to about 0° C. and a solution of 5% HCl is added until reaching a pH value from 1 to 2. The biphasic solution is then concentrated under reduced pressure and the formed solid filtered off and washed with water until reaching a neutral pH value. The product is dried in an oven providing 94 g of 2-bromo-5-hydroxy-benzyl alcohol of formula (III) with a yield of 93%. $^1$H-NMR (DMSO-d$_6$, 300 MHz) δ (ppm): 9.59 (1H, s), 7.27 (1H, d, J=8.7 Hz), 6.97 (1H, d, J=3.3 Hz), 6.55 (1H, dd, J=3.3, J=8.7), 5.33 (1H, t, J=5.7 Hz), 4.38 (2H, d, J=5.7 Hz).

Example 2: Synthesis of 1-Bromo-4-Trimethylsilanoxy-2-Trimethylsilanoxymethyl benzene of Formula
(III)

20.0 g (98.3 mmol) of 2-bromo-5-hydroxy-benzyl alcohol of formula (III), obtained as described in Example 1, are dissolved under nitrogen in 120 mL of toluene and 32.8 g (325 mmol) of triethylamine. The solution is cooled down to 0° C. and 23.5 g (216 mmol) of trimethylsilyl chloride are added maintaining the temperature below 15° C. At the end of the addition, the mixture is allowed to reach room temperature, 50 mL of water is added and the phases are separated. The organic phase is concentrated to dryness under reduced pressure to obtain 34.8 g of 1-bromo-4-trimethylsilanoxy-2-trimethylsilanoxymethyl benzene of formula (III) as a dark oil with a yield of 97%. The crude reaction product is used in the next step without any further purification. $^1$H-NMR (CDCl$_3$, 300 MHz) δ (ppm): 7.31 (1H, d, J=8.4 Hz), 6.97 (1H, m), 6.55 (1H, dd, J=3.3, J=8.4 Hz), 4.63 (2H, s), 0.26 (9H, s), 0.18 (9H, s).

Example 3: Synthesis of
4-(4-Bromo-3-hydroxymethyl-phenoxy)-benzonitrile
of Formula (II)

27.1 g (197 mmol) of K$_2$CO$_3$, 12.13 g (100.3 mmol) of 4-fluorobenzonitrile of formula (IV), 34.2 g (98.3 mmol) of 1-bromo-4-trimethylsilanoxy-2-trimethylsilanoxymethyl benzene of formula (III), obtained as described in Example 2, and 60 mL of DMSO are placed under nitrogen in a previously anhydrified flask. The reaction mixture is heated to 105° C. and kept at the same temperature for 2 hours. Then, 120 mL of toluene and 240 mL of $H_2O$ are added, the phases are separated and the organic phase is washed with a solution of 10% $K_2CO_3$. The organic phase is allowed to cool down to room temperature and the product is allowed to crystallize providing 19.7 g 4-(4-bromo-3-hydroxymethyl-phenoxy)-benzonitrile of formula (II) with a yield of 66%. $^1$H-NMR (DMSO-$d_6$, 300 MHz) δ (ppm): 7.85-7.80 (2H, m) 7.62 (1H, d, J=8.4 Hz), 7.22 (1H, d, J=3.0 Hz), 7.13-7.11 (2H, m) 6.98 (1H, dd, J=3.0, J=8.4 Hz), 4.47 (2H, s).

Example 4: Synthesis of 4-(4-Bromo-3-hydroxymethyl-phenoxy)-benzonitrile of Formula (II)

27.2 g (197 mmol) of $K_2CO_3$, 11.9 g (98.5 mmol) of 4-fluorobenzonitrile of formula (IV), 20.0 g (98.5 mmol) of 2-bromo-5-hydroxy-benzyl alcohol of formula (III), obtained as described in Example 1, and 80 mL of DMSO are placed under nitrogen in a previously anhydrified flask. The mixture is heated to 125° C. and maintained at said temperature for 4 hours. 240 mL of $H_2O$ are added and the precipitate is filtered off and washed with $H_2O$ until reaching a neutral pH value. The solid is dried and analyzed by HPLC (yield of 70%). The mixture is then dissolved in 70 mL hot toluene and allowed to crystallize while cooling the solution down to room temperature obtaining 16.3 g of 4-(4-bromo-3-hydroxymethyl-phenoxy)-benzonitrile of formula (II) with a yield of 54%. $^1$H-NMR (DMSO-$d_6$, 300 MHz) δ (ppm): 7.85-7.80 (2H, m) 7.62 (1H, d, J=8.4 Hz), 7.22 (1H, d, J=3.0 Hz), 7.13-7.11 (2H, m) 6.98 (1H, dd, J=3.0, J=8.4 Hz), 4.47 (2H, s).

Example 5: Synthesis of 4-(4-Bromo-3-Trimethylsilanoxymethyl)-benzonitrile of Formula (II)

40.0 g (131 mmol) of 4-(4-bromo-3-hydroxymethyl-phenoxy)-benzonitrile of formula (II), prepared as described in Example 3, are added under nitrogen to 400 mL THF and 23.8 g (236 mmol) of triethylamine in a previously anhydrified flask. The solution is cooled down to 0° C. and 16.9 g (157 mmol) of trimethylsilyl chloride are added maintaining the temperature below 15° C. After completion of the addition, the mixture is allowed to reach room temperature. 50 mL of toluene and 100 mL of water are added and the phases are separated. The organic phase is washed with a saturated NaCl solution and evaporated to dryness under reduced pressure to obtain 49.4 g of 4-(4-bromo-3-trimethylsilanoxymethyl)-benzonitrile of formula (II) as a solid with a yield of 98%. The obtained product is used in the next step any without further purification. $^1$H-NMR (CDCl$_3$, 300 MHz) δ (ppm): 7.63-7.60 (2H, m) 7.52 (1H, d, J=8.4 Hz), 7.22 (1H, m) 7.03-7.00 (2H), 6.85-6.80 (1H, m) 4.69 (2H, s), 0.17 (9H, s).

Example 6: Synthesis of 4-((1-Hydroxy-1,3-dihydrobenzo[c][1,2]oxaborol-5-yl)oxy)benzonitrile (Crisaborole) of Formula (I)

83.0 g (220 mmol) of 4-(4-bromo-3-trimethylsilanoxymethyl)-benzonitrile of formula (II), prepared as described in Example 5, 540 mL THF and 62.0 g (330 mmol) of B(OiPr)$_3$ are added under nitrogen in a previously anhydrified flask. The mixture is cooled down to −78° C. and then 86 mL of a 2.3 M solution of hexyllithium in hexane is added keeping the temperature below −75° C. After the addition of hexyllithium, the solution is maintained for one further hour at a temperature below −78° C. and then allowed to reach room temperature. A solution of 5% HCl is added until reaching a pH value from 1 to 2. The two phases are separated and the organic phase is concentrated to residue. The residue is dissolved in 240 mL of toluene, then 40 mL of water are added resulting in the formation of solid Crisaborole. The mixture is cooled down to 0° C. and stirred for 10 hours. The solid is then filtered off and washed with toluene providing 42 g of Crisaborole of formula (I) with a yield of 82%. $^1$H-NMR (DMSO-$d_6$, 300 MHz) δ (ppm): 9.18 (1H, s), 7.85-7.80 (2H, m) 7.76 (1H, d, J=8.1 Hz), 7.14-7.11 (3H, m), 7.07 (1H, dd, J=2.1, J=8.1 Hz), 4.95 (2H, s).

Example 7: Comparison Between the Synthesis of 4-(4-Bromo-3-hydroxymethyl-phenoxy)-Benzonitrile of Formula (II) Obtained by the Method of the Present Invention and by the Method of Biorg. Med. Chem. Lett. 2009, 19, 2129-2132

4-(4-Bromo-3-hydroxymethyl-phenoxy)-benzonitrile of formula (II) has been prepared starting from 2-bromo-5-hydroxy benzaldehyde of formula (VII) according to the preparation described in Biorg. Med. Chem. Lett. 2009, 19, 2129-2132 and the procedure of the present invention.

As shown in Table 1 below, the procedure of the present invention results in a reduction of the reaction steps from 4 to 2 or 3, eliminating some of the protection/deprotection steps of the procedure described in Biorg. Med. Chem. Lett. 2009, 19, 2129-2132. At the same time the process of the present invention allows to reduce the number of used reagents.

TABLE 1

| Process | Number of Steps | Number of Steps protection/deprotection |
| --- | --- | --- |
| Biorg. Med. Chem. Lett. 2009, 19, 2129-2132 | 4 | 2 |
| Present invention with P and W = hydrogen | 2 | 0 |
| Present invention with P and W = trimethylsilyl | 3 | 1 |

Example 8: Comparison Between the Synthesis of Crisaborole of Formula (I) Obtained by the Method of the Present Invention and by the Method of Biorg. Med. Chem. Lett. 2009, 19, 2129-2132

The intermediate used in the preparation of Crisaborole of Biorg. Med. Chem. Lett. 2009, 19, 2129-2132 has the alcoholic group protected with tetrahydropyranyl (THP), while in the present invention the benzyl alcohol is protected with a silyl group.

As shown in Table 2, the silyl protected intermediate allows to obtain Crisaborole of formula (I) at significantly higher yields than starting from the THP-protected alcohol.

TABLE 2

| Process | Intermediate | Crisaborole of Formula (I) [yield %] |
|---|---|---|
| Biorg. Med. Chem. Lett. 2009, 19, 2129-2132 | 6 | 33-44% |
| Present invention | (II) | 82-93% |

Example 9: Crisaborole in Crystalline Form 1

1.0 g of Crisaborole is fully dissolved in a mixture of ethyl acetate/methanol (1:1, v.v). The solution is concentrated and the residual oil solidifies slowly overnight. The residue is then treated with a mixture of hexane/ethyl acetate (9:1, v:v) and stirred for 48 hours at approximately 40° C. The suspension is then filtered off and the obtained solid rinsed with hexane providing 0.8 g of Crisaborole in crystalline Form 1 having an XRPD spectrum, wherein the most intense peaks are observed at about 6.0, 12.1, 14.1, and 15.4±0.2° in 2θ (FIG. 1). The HPLC purity is about equal to 99.88% at 220 and 254 nm.

Example 10: Crisaborole Methyl Ester in Crystalline Form α

75.0 g of Crisaborole are fully dissolved at 60° C. to 65° C. in 900 ml of methanol. The yellow solution is kept at 60° C. to 65° C. for 30 minutes, then cooled down to 50° C. to 55° C. and maintained under these conditions for 15 to 30 minutes. The mixture is then concentrated to about half the initial volume and cooled down to 0° C. to 5° C. The suspension is filtered off and the solid washed with methanol providing 72.0 g of Crisaborole methyl ester in crystalline Form α with a HPLC purity >99.50% (254 nm) and wherein the most intense peaks (expressed in ° in 2θ) are observed at about 7.4, 12.2, 13.0, 14.1, 16.2, 17.6, 18.8, 19.8, 24.7, 25.5, and 26.6±0.2°.

$^1$H-NMR (300 MHz, CDCl$_3$) δ (ppm): 7.73 (d, J=7.8 Hz, 1H), 7.62 (d, J=8.7 Hz, 2H), 7.26-6.99 (m, 4H), 5.07 (s, 2H), 3.89 (s, 3H).

Example 11: Crisaborole Methyl Ester in Crystalline Form α

The process as described in Example 10 can be also performed by adding a previously obtained seed of Crisaborole methyl ester in crystalline Form α to the reaction mixture at 50° C. to 55° C. The mixture is maintained at these conditions for about 15 to 30 minutes, then concentrated to about half the initial volume and cooled down to 0° C. to 5° C. The suspension is then filtered off and the obtained solid washed with methanol.

Example 12: Crisaborole in Crystalline Form 1

72.0 g of Crisaborole methyl ester in crystalline Form α obtained as disclosed in Examples 10 or 11 are suspended in 1500 ml of water at 15° C. to 20° C. The suspension is stirred for 2 hours, and then the solid is filtered off, washed with water and dried under vacuum at about 50° C. providing 65.1 g of Crisaborole crystalline Form 1 with a HPLC purity of >99.50% at 220 nm.

Example 13: Crisaborole Isopropyl Ester 1.00 g of Crisaborole is dissolved at reflux in 10 mL of isopropanol. The solvent is then removed at reduced pressure giving 1.16 g Crisaborole isopropyl ester as a white crystalline solid. $^1$H-NMR (300 MHz, DMSO-d$_6$) δ (ppm): 7.84 (d, J=8.7 Hz, 2H), 7.69 (d, J=8.1 Hz, 1H), 7.16-7.06 (m, 4H), 5.03 (s, 2H), 4.76-4.68 (m, 1H), 1.26 (d, J=6.0 Hz, 6H).

The following compounds can be analogously prepared according to the procedure for Crisaborole isopropyl ester:
Crisaborole ethyl ester;
Crisaborole propyl ester; and
Crisaborole butyl ester

Example 14: Crisaborole in Crystalline Form 1

Crisaborole ethyl ester, Crisaborole propyl ester, Crisaborole isopropyl ester and Crisaborole butyl ester, as obtained in Example 13, can be converted into Crisaborole crystalline Form 1 according to the procedure disclosed in Example 12.

What is claimed is:

1. A process for preparing Crisaborole in crystalline form 1 having an XRPD spectrum comprising peaks falling at 6.0, 12.1, 14.1, and 15.4±0.2° in 2θ, said process comprising:
   i) hydrolyzing Crisaborole C$_1$-C$_5$ alkyl ester of formula (X)

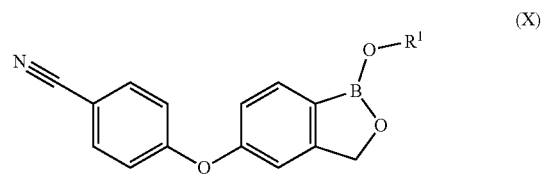

wherein R$^1$ is a C$_1$-C$_5$ alkyl group.

2. The process for preparing Crisaborole in crystalline form 1 according to claim 1, wherein the Crisaborole C$_1$-C$_5$ alkyl ester of formula (X) is Crisaborole methyl ester of crystalline form α having an XRPD spectrum, wherein characteristic peaks fall at about 14.1, 16.2, 19.8, 24.7, and 26.6±0.2° in 2θ, or Crisaborole isopropyl ester.

3. The process for preparing Crisaborole in crystalline form 1 according to claim 1, wherein the Crisaborole C$_1$-C$_5$ alkyl ester of formula (X) is prepared by a process comprising:
   ii) forming a solution of Crisaborole in a C$_1$-C$_5$ alcohol or in a solvent mixture comprising a C$_1$-C$_5$ alcohol;
   iii) cooling and/or concentrating the solution and recovering Crisaborole C$_1$-C$_5$ alkyl ester of formula (X).

4. The process according to claim 3, wherein the Crisaborole C$_1$-C$_5$ alkyl ester of formula (X) is Crisaborole methyl ester of crystalline form α having an XRPD spectrum with characteristic peaks at about 14.1, 16.2, 19.8, 24.7, and 26.6±0.2° in 2θ or Crisaborole isopropyl ester.

5. The process according to claim 3, wherein the formation of Crisaborole C$_1$-C$_5$ alkyl ester of formula (X) in steps ii) and iii) is carried out under anhydrous conditions.

6. The process according to claim 3, wherein a previously obtained seed crystal of Crisaborole $C_1$-$C_5$ alkyl ester of formula (X) is added in step iii).

7. The process according to claim 3, wherein Crisaborole of step ii) is prepared by a process comprising reacting a compound of formula (II),

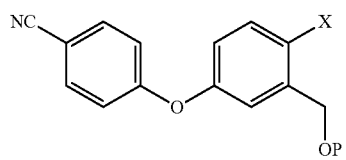

wherein X is a halogen atom,
P is hydrogen or a protective group of the hydroxyl group;
with a boric ester in a solvent and with a strong base.

8. The process according to claim 7, wherein P is hydrogen or a silyl group.

9. The process according to claim 7, wherein a compound of formula (II) is prepared by a process
comprising reacting a compound of formula (III)

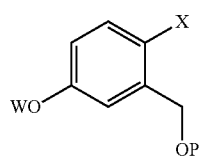

wherein X and P are as defined in claim 7, and
W is hydrogen or a protective group of the phenolic functionality;
with a compound of formula (IV)

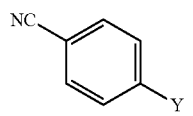

wherein Y is a halogen atom,
in the presence of a base and optionally a solvent;
and, if the case, converting a compound of formula (II) into another compound of formula (II).

10. Crisaborole $C_1$-$C_5$ alkyl ester of formula (X)

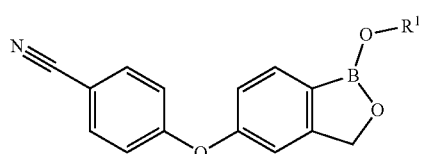

wherein $R^1$ is a $C_1$-$C_5$ alkyl.

11. Crisaborole $C_1$-$C_5$ alkyl ester of formula (X) as defined in claim 10, selected from:
Crisaborole methyl ester,
Crisaborole ethyl ester,
Crisaborole propyl ester,
Crisaborole isopropyl ester, or
Crisaborole butyl ester.

12. Crisaborole $C_1$-$C_5$ alkyl ester of formula (X) as defined in claim 10, selected from:
Crisaborole isopropyl ester or
Crisaborole methyl ester in crystalline form α having an XRPD spectrum with characteristic peaks at 14.1, 16.2, 19.8, 24.7, and 26.6±0.2° in 2θ.

13. A process for preparing a pharmaceutical composition comprising Crisaborole of formula (I)

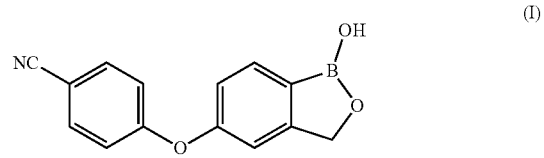 [SMILES: N#Cc1ccc(Oc2ccc3c(c2)COB3O)cc1]

and at least one pharmaceutically acceptable carrier or vehicle, said process comprising:
hydrolizing Crisaborole $C_1$-$C_5$ alkyl ester of formula (X) to Crisaborole in crystalline form 1 according to claim 1 and
formulating Crisaborole in crystalline form 1 together with at least one pharmaceutically acceptable carrier or vehicle.

14. The process according to claim 13, wherein Crisaborole in crystalline form 1 is formulated by mixing.

15. The process according to claim 13, wherein the pharmaceutical composition comprises compounds of formula (VIII) or (IX)

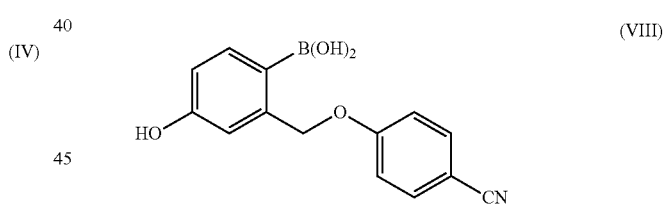

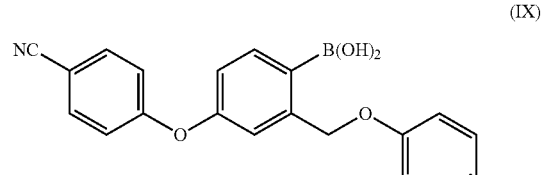

as impurities in a percentage equal to or less than 0.1% compared to Crisaborole of formula (I) and evaluated by HPLC at 254 nm.

16. The process according to claim 13, wherein the pharmaceutical composition is a topical composition.

* * * * *